United States Patent [19]
Becker et al.

[11] Patent Number: 5,534,474
[45] Date of Patent: Jul. 9, 1996

[54] PROCESS FOR PREPARING ALUMINOXANE ON INERT SUPPORT MATERIAL

[75] Inventors: Ralf-Jürgen Becker, Hamm; Stefan Gürtzgen, Wuppertal; Dirk Kutschera, Dortmund, all of Germany

[73] Assignee: Witco GmbH, Bergkamen, Germany

[21] Appl. No.: 402,899

[22] Filed: Mar. 13, 1995

[30]  Foreign Application Priority Data

Mar. 18, 1994 [DE] Germany .................. 44 09 249.0

[51] Int. Cl.⁶ .................. B01J 37/02; C07F 5/06
[52] U.S. Cl. .................. 502/152; 502/111; 502/156; 556/179
[58] Field of Search .................. 502/111, 117, 502/152, 156; 556/179

[56]  References Cited

U.S. PATENT DOCUMENTS

| | | | |
|---|---|---|---|
| 4,921,825 | 5/1990 | Kioka et al. | 502/104 |
| 5,015,749 | 5/1991 | Schmidt et al. | 556/179 |
| 5,026,797 | 6/1991 | Takahashi | 526/124 |
| 5,086,025 | 2/1992 | Chang | 502/117 |
| 5,234,878 | 8/1993 | Tsutsui et al. | 502/103 |

FOREIGN PATENT DOCUMENTS

| | | |
|---|---|---|
| 0369675 | 5/1990 | European Pat. Off. |
| 0442725 | 8/1991 | European Pat. Off. |

OTHER PUBLICATIONS

Chien, et al. (1991) "Olefin Copolymerization with Metallocene Catalysts. III. Supported Metallocene/Methylaluminoxane Catalyst for Olefin Copolymerization", *Journal of Polymer Science: Part A: Polymer Chemistry* 29, 1603–1607. (month unknown).

Kaminsky, et al. (1986) "Olefinpolymerization with Highly Active Soluble Zirconium Compounds using Aluminoxane as Co-catalyst", *Makromol. Chem. Macromol. Symp.* 3, 377–387. (month unknown).

*Primary Examiner*—Shrive Beck
*Assistant Examiner*—Timothy H. Meeks
*Attorney, Agent, or Firm*—Scully, Scott, Murphy & Presser

[57]  ABSTRACT

The invention relates to a process for preparing alkylaluminoxanes immobilized on inert support materials from alkylaluminum compounds and water, which is characterized in that the reactants are metered with the gas stream into a fluidized-bed reactor and the reaction product is fixed on the support directly from the gas phase.

11 Claims, 2 Drawing Sheets

PROCESS FOR PREPARING ALUMINOXANE ON INERT SUPPORT MATERIAL

BACKGROUND OF THE INVENTION

Alkylaluminoxanes, in particular methylaluminoxane, are becoming increasingly important as an essential constituent of a new generation of catalyst systems for preparing polyolefins (single site catalysts). These new catalysts consist essentially, as is already known from the classical Ziegler-Natta catalysis, of a transition metal compound as catalyst and the alkylaluminoxane as organoaluminum cocatalyst component. Transition metal compounds which are preferably used are cyclopentadienyl, indenyl or fluorenyl derivatives of metals in group IVa of the Periodic Table (IUPAC notation). In contrast to conventional Ziegler-Natta catalysts, such systems not only possess, besides high activity and productivity, the ability to control the product properties as a function of the components used and the reaction conditions, but they additionally make accessible hitherto unknown polymer structures having promising properties with regard to industrial applications.

Many publications have appeared in the literature, which deal with the preparation of specific polyolefins using such catalyst systems. However, a disadvantage in virtually all cases is the fact that to achieve acceptable productivities, a high excess of alkylaluminoxanes is required, based on the transition metal component (the ratio of aluminum in the form of the alkylaluminoxane to transition metal is usually about 1,000:1). Owing to the high price of the alkylaluminoxanes on the one hand, and, on the other hand, additional polymer workup steps (such as deashing steps) required in some cases, polymer production on an industrial scale on the basis of such catalyst systems would often be uneconomical. In addition, the solvent toluene often used for the formulation of alkylaluminoxanes, in particular methylaluminoxane, is increasingly undesirable both for reasons of storage stability of the formulations (strong tendency towards gel formation) and with regard to the application of the polyolefins finally produced.

A significant reduction in the amount of alkylaluminoxane required in relation to the transition metal component can be achieved by applying alkylaluminoxane to inert support materials, preferably $SiO_2$ (J. C. W. Chien, D. He, J. Polym. Science Part A, Polym. Chem., Vol. 29, 1603–1607 (1991). Such supported materials additionally possess the advantage of being easily separated off in polymerizations in the condensed phase (preparation of high-purity polymers) or being able to be used as freeflowing powders in modern gas-phase processes, with the particle morphology of the polymer being able to be predetermined directly by the particle shape of the support. Furthermore, alkylaluminoxanes fixed on supports are, as dry powders, physically more stable than solutions having a comparable Al content. This is particularly true of methylaluminoxane which, as already mentioned, tends towards gel formation in toluene solution after a certain storage time.

A number of possibilities for fixing alkylaluminoxanes on supports have already been described in the literature.

EP 0 369 675 (Exxon Chemical) describes a process in which the immobilization of alkylaluminoxanes is achieved by reaction of an about 10% strength solution of trialkylaluminum in heptane with hydrated silica (8.7% by weight $H_2O$).

EP 0 442 725 (Mitsui Petrochemical) effects the immobilization by reaction of a toluene/water emulsion with an about 7% strength solution of trialkylaluminum in toluene in the presence of silica at temperatures of from −50° C. to +80° C.

A further alternative is offered by U.S. Pat. No. 5,026,797 (Mitsubishi Petrochemical) by reaction of prepared alkylaluminoxane solutions with silica (predried at 600° C.) at 60° C. and subsequent washing out of the proportion of alkylaluminoxane not immobilized by means of toluene.

Finally, U.S. Pat. No. 4,921,825 (Mitsui Petrochemical) describes a process for immobilizing alkylaluminoxane by precipitation from toluene solution by means of n-decane in the presence of silica.

These processes are sometimes technically complicated, since they comprise, inter alia, low reaction temperatures at the beginning, or multistage workup processes, thus resulting in yield losses with regard to the amount of aluminum used in the form of aluminum trialkyls. In addition, the space-time yield is sometimes considerably impaired by the obligatory use of relatively high amounts of solvent.

It is therefore an object of the present invention to overcome these disadvantages of the prior art and to provide an economical process by means of which alkylaluminoxanes can, without use of organic solvents, be fixed on inert support materials in high yield and homogeneity in a reproducible manner, with the particle morphology of the support being retained and the products being finally obtained as free-flowing powders.

BRIEF SUMMARY OF THE INVENTION

Figure 1:
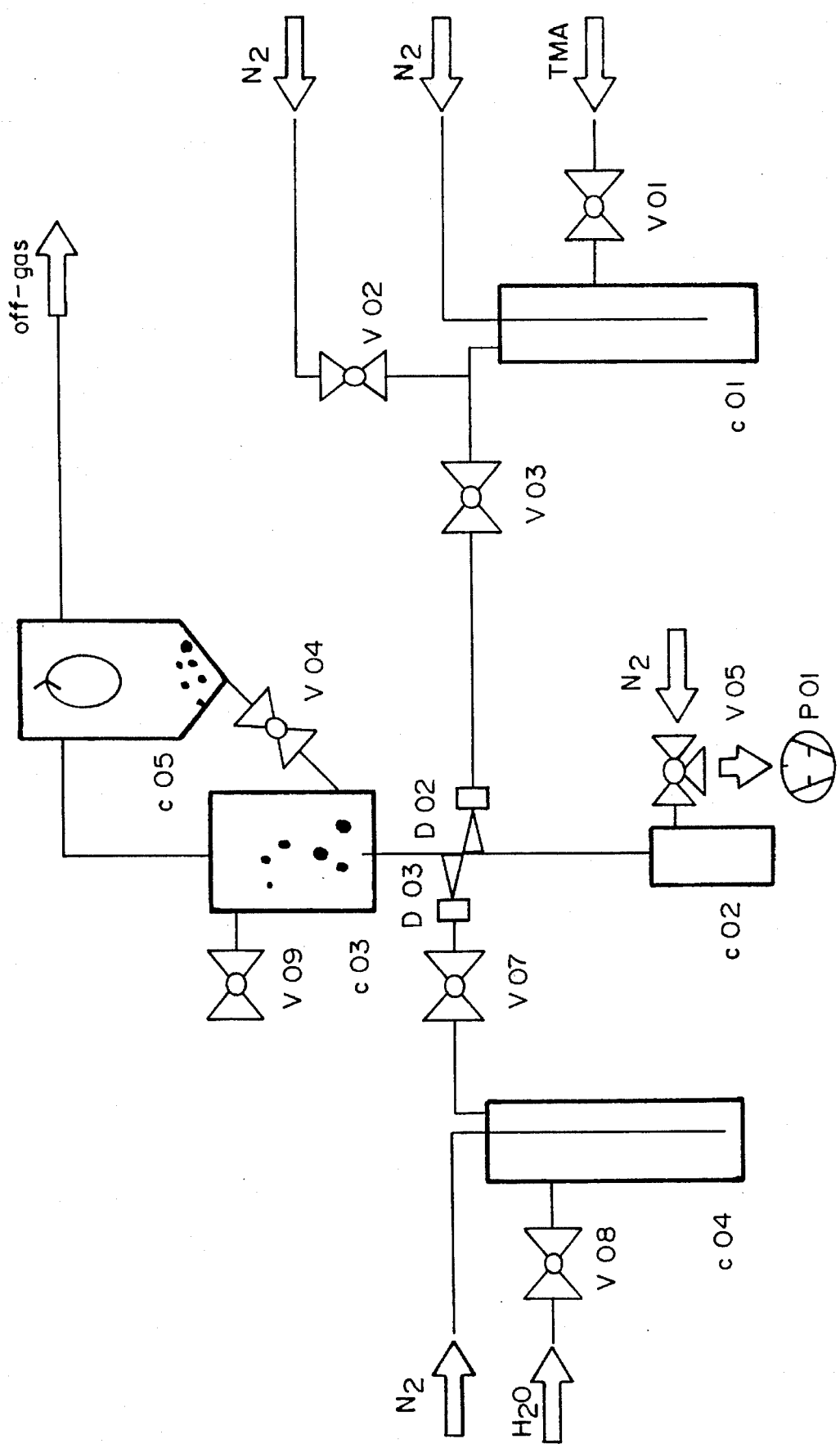
FIG. 1 is a flowsheet depicting schematically one embodiment of the process of the present invention.

It has now surprisingly been found that all the abovementioned disadvantages can be eliminated by carrying out the synthesis of alkylaluminoxanes, in particular methylaluminoxane (MAO), and their fixing on inert supports directly via the gas phase without any use of solvents and without additional process steps. The end product obtained is characterized by being a free-flowing powder.

The present invention accordingly provides a process for preparing one or more alkylaluminoxanes fixed on solid, particulate inert support material from one or more alkylaluminum compounds and water, comprising metering said one or more alkylaluminum compounds in one or more atomized or gaseous feed streams into a fluidized bed reactor containing therewithin said solid, particulate inert support material while maintaining said support material under fluidizing conditions with an inert gas stream, and providing water in said reactor, whereby said one or more alkylaluminum compounds and water react and form said one or more alkylaluminoxanes on said support material directly in said inert gas stream.

The invention further provides aluminoxanes fixed on support materials, prepared according to the process of the invention.

Further subject matter of the invention is characterized by the claims.

DETAILED DESCRIPTION OF THE INVENTION

The preparation is carried out by generally known fluidized-bed processes. A fluidized bed means a finely particulate bed of solids which is agitated by fluid flowing through the solids to such an extent that the particles can change position over a certain path (Walter Wagner Kamprath, Reihe Technik, Wärmeübertrag, 2nd edition, Würzburg, Verlag Vogel, 1988, page 143).

Distinction is here made between a stationary and circulating fluidized bed (Dieter, Onken, Leschonski, Grundzüge der mechanischen Verfahrenstechnik, 1st edition, München; Wien: Verlag Hanser 1986, Pages 40–47, 298–300).

According to the process of the invention, the fluidized beds are maintained by means of continuously flowing inert gas streams. The pressure within the fluidized bed reactor can be selected within wide limits and depends on the requirements.

In fluidized-bed reactors, solid particles are fluidized by a rising gas stream. The solid can here serve as catalyst or as reactant (Vauck, Müller, Grundoperationen chemischer Verfahrenstechik, 8th edition, New York; Weinheim: VCH Verlagsgesellschaft mbH, page 230).

The solid particles and the gas phase can be continuously replaced during operation.

Furthermore, the fluidized bed can be maintained by means of the recirculated alkanes obtained as reaction products, if these are present in gaseous form under the given reaction conditions.

The metering of the reactant trialkylaluminum, in particular trimethylaluminum (TMA), and the providing of the water into the fluidized-bed reactor, can be carried out via the gas streams used. Regulation of the respective gas streams allows both the degree of oligomerization (n) of the alkylaluminoxane product and the degree of loading of the support to be controlled systematically. In the case of suitable support materials such as, for example, $SiO_2$, the reactant water can in addition (or instead) be provided in the form of water bound to the surface of the support.

The direct feeding of trialkylaluminum, in particular trimethylaluminum (TMA), and water into the gas phase (wherein the only gas stream introduced into the reactor is that which serves solely to maintain the fluidized bed) and continuous operation of the plant are also possible. In all cases, the original particle morphology of the support is retained.

To prepare the aluminoxanes, the molar ratio of water to alkylaluminum compounds can lie within ranges from 0.5:1 to 1.3:1, preferably from 0.9:1 to 1.2:1.

Furthermore, the mean degree of oligomerization n, which is expressed by the mean molecular weight of the reaction product, can be influenced in a targeted way by appropriate metering in of the reactants and control of the reaction parameters. Thus, the molar ratio $H_2O$/trialkylaluminum, particularly in the case of TMA, can be set to the desired value. This is of particular importance, since the activity of aluminoxanes as cocatalyst in olefin polymerization is apparently dependent on the degree of oligomerization of the aluminoxane used (Ref.: W. Kaminsky, Nachr. Chem. Tech. Lab. 29, 373–7 (1981); W. Kaminsky et al., Makromolo Chem., Macromol. Symp. 3, 377–87 (1986)).

Organoaluminum compounds which can be used are in principle all the compounds customary in this field which can be hydrolyzed with water to give aluminoxanes. Accordingly to the invention, trialkylaluminum compounds with which the process of the present invention is particularly useful correspond to the formula $(R)_3Al$ wherein each R is a straight or branched alkyl group containing 1 to 10, and preferably 1 to 5, carbon atoms. Preferably, all three R groups are the same. Preferred alkyl groups include methyl, ethyl, propyl, isopropyl, butyl, isobutyl, tert-butyl and pentyl. Trimethyl aluminum is especially preferred.

The support materials used according to the invention are the porous oxides of one or more elements of the groups II, III or IV or the Periodic Table, such as $ZrO_2$, $TiO_2$, $B_2O_3$, CaO, ZnO, BaO, preferably $Al_2O_3$ and MgO and in particular $SiO_2$.

These support materials can have particle sizes in the range of 1–300 microns, preferably 10–200 microns; surface areas of 10–1000 $m^2/g$, in particular 100–500 $m^2/g$; $N_2$ pore volumes of 0.5–3 $cm^3$, preferably 1–2 $cm^3$.

These supports are commercial materials which contain the specified values in a random distribution.

The water content of the support materials can, depending on the process procedure, vary between about 0 and 15% by weight. The desired water contents can be set by the generally known hydration methods or calcination methods from commercial support materials.

The ratio of support to aluminoxane can be varied within relatively wide limits; according to the invention it is selected so that 3–40% by weight, preferably 5–25% by weight, of aluminum is present in the form of aluminoxanes on the resulting free-flowing powder of support material and aluminoxane.

The process of the invention makes possible the preparation of supported aluminoxanes with almost quantitative yields of immobililzed aluminum, based on trialkylaluminum compounds used. Owing to the reproducible process conditions which can be set in a targeted manner, these supported alkylaluminoxanes, in particular the methylaluminoxane, prepared using the process of the invention have high activities as cocatalysts and are thus outstandingly suitable for the further preparation of catalyst system for olefin polymerization.

The process of the invention is illustrated below by means of the following examples. The values of the process variables temperature, pressure and volume flow given in the examples are values averaged over the entire experiment. The experiments were carried out in such a way that these mean values lay within the preferred range.

The process parameters can, within the specified minima and maxima, be utilized for varying or optimizing products.

| General specification of reaction parameters in carrying out the process of the invention. | | |
|---|---|---|
| Mass of support: | max. | 30.0 g |
|  | min. | 10.0 g |
|  | preferred range | 15.0 g–25.0 g |
| Temperature: | min. | 2° C. |
|  | max. | 90° C. |
|  | preferred range | 20° C.–60° C. |
| Delta T in the | min. | 10° C. |
| reaction | max. | 30° C. |
|  | preferred range | 20° C.–25° C. |
| Pressure: | | |
| Pressure fluctuations result from the type of fluidized bed and the degree of loading. | | |
|  | min. | 0.5 bar |
|  | max. | 20 bar |
|  | preferred range | 1 bar–1.5 bar |
| Volume flows: | | |
| Formation of the | max. | 13 liter/min |
| fluidized bed: | min. | 6 liter/min |
|  | preferred range | 8 liter/min–10 |

-continued

General specification of reaction parameters in carrying out the process of the invention.

|  |  | liters/min |
|---|---|---|
| Formation of the circulating fluidized bed: | | |
|  | max. | 20 liter/min |
|  | min. | 14 liter/min |
|  | preferred range | 16 liter/min–18 liters/min |
| laden with TMA: | max. | 1 liter/min |
|  | min. | 0.2 liter/min |
|  | preferred range | 0.3 liter/min–0.8 liter/min |
| laden with H$_2$O: | max. | 1 liter/min |
|  | min. | 0.2 liter/min |
|  | preferred range | 0.3 liter/min–0.8 liter/min |
| Volume flow ratio for off-gas recirculation: | | |
| $\frac{V\ N_2\ (new)}{V\ (off\text{-}gas)}$ | max. | 0.5 |
|  | min. | 0.05 |
|  | preferred range | 0.1–0.3 |
| Reaction time: | min. | 20 min |
|  | max. | 120 min |
|  | preferred range | 30 min–90 min |

The following Examples make reference to the FIGS. 1 and/or 2, in which the respective reference numerals have the following meaning:

| Reference Numeral | Description |
|---|---|
| C 01 | Metering container for trialkylaluminum (TMA) |
| C 02 | Container for receiving product obtained from reaction in fluidized bed reactor |
| C 03 | Fluidized bed reactor |
| C 04 | Metering container for water |
| C 05 | Cyclone or equivalent separator for separating contained solids from gas stream |
| V 01 | Valve on trialkylaluminum (TMA) feed line |
| V 02 | valve on inert gas (N$_2$) feed line |
| V 03 | Valve on line feeding inert gas/ trialkylaluminum stream to reactor |
| V 04 | Valve on line feeding solids from container C 05 to reactor C 03 |
| V 05 | Valve on line feeding inert fluidizing gas (N$_2$) to reactor C 03 |
| V 07 | Valve on line feeding water (and inert gas (N$_2$)) to reactor C 03 |
| V 08 | Valve on line feeding water to metering container C 04 |
| v 09 | Valve on line feeding particulate solid support material to reactor C 03 |
| P 02 | Compressor for recirculating line to reactor C 03 |

EXAMPLES

Example 1: (Simultaneous metering is via separate gas streams)

Referring to FIG. 1, all valves were closed in the initial position. The solid particulate support material (silica gel, "SD 3216–30", Grace GmbH) was initially charged into fluidized bed reactor C 03 via valve V 09. To form a fluidized bed, valve V 05 was opened and N$_2$ was fed in. The solids separated out in separator C 05 were fed back into C 03 via valve V 04.

TMA was fed into the metering container C 01 via valve V 01 and H$_2$O was fed into the metering container C 04 via valve V 08.

First, an inert gas steam (N$_2$) fed into the system via valve V 02 was laden with trimethylaluminum (TMA) from container C 01 and the resulting stream was passed into the reaction container C 03 via valve V 03. When the fluidized bed had stabilized, a second inert gas stream laden with H$_2$O was fed to C 03 via valve V 07.

After the reaction time, the additions of TMA and H$_2$O were stopped by closing the valves V 07 and V 03. By closing valve V 05, the fluidized bed was discontinued and the product fell into C 02.

| Reaction parameters | |
|---|---|
| Support: | Surface area by N$_2$-BET = 316 m$^2$/g; particle size distribution = 20–80 microns; N$_2$ pore volume = 1.55 ml/g |
| Mass of support: | 18.3 g |
| Reactor volume: | 2 l |
| Volume flow of N$_2$ (formation of the fluidized bed): | 8.31 liter/min |
| Volume flow of N$_2$ (laden with TMA): | 0.51 liter/min |
| Volume flow of N$_2$ (laden with H$_2$O): | 0.51 liter/min |
| Reaction time: | 90 min |

The product obtained had an Al content of 6.6% by weight and a methyl/Al ratio of 0.96.

Example 2

The experiment was carried out in a similar way to Example 1, except that 22.6 g of support were used and the reaction time was 30 min.

The Al content of the product was 3.2% by weight and the methyl/Al ratio was 0.96.

Example 3: (Reactant H$_2$O on support in absorbed form)

The experiment was carried out in a similar way to Example 1, except that 19 g of the same support but containing 2.6% by weight of water were added. Since an additional metering of H$_2$O was therefore not to be carried out, valve V 07 remained closed over the entire time of the experiment.

After a reaction time of 30 minutes a product was recovered which had an Al content of 2.6% by weight and a methyl/Al ratio of 0.98.

Example 4: (Recirculation of the off-gases)

Figure 2:
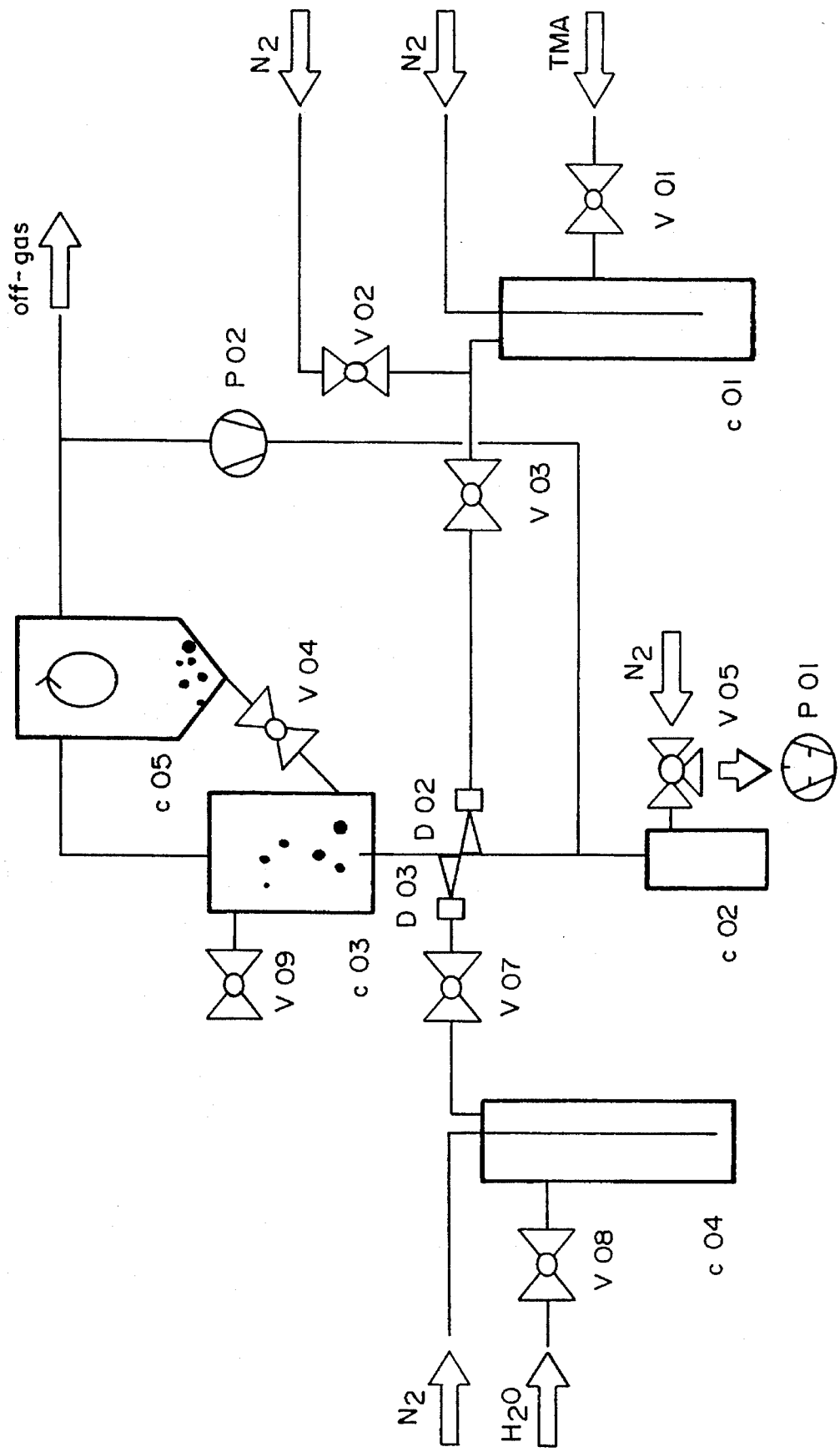
FIG. 2 is a flowsheet depicting schematically another embodiment of the process of the present invention.

Referring to FIG. 2, all valves were closed in the initial position. The solid was initially charged into C 03 via valve V 09. To form a fluidized bed, valve V 05 was opened and N$_2$ was passed in. The solids separated off in separator C 05 were again fed into C 03 via valve V 04.

TMA was fed into the metering container C 01 via valve V 01 and H$_2$O was fed into the metering container C 04 via valve V 08.

First, an inert gas stream ($N_2$) fed into the system via valve V 02 was laden with trimethylaluminum (TMA) from container C 01 and the resulting stream was passed into the reaction container C 03 via valve V 03. When the fluidized bed had stabilized, a second inert gas stream laden with $H_2O$ was fed to C 03 via valve V 07.

The compressor P 02 for recirculating the offgases was switched on and the volume flow of $N_2$ for forming the fluidized bed was simultaneously reduced. After the reaction time, the compressor P 02 was switched off and the additions of TMA and $H_2O$ were stopped by closing the valves V 07 and V 03. The fluidized bed was discontinued by closing valve V 05 and the product fell into C 02.

The reaction parameters were similar to Example 1 with the following exceptions:

| | |
|---|---|
| Mass of support | 21.1 g |
| Volume flow of $N_2$ (formation of the fluidized bed): | 17.2 l/min |
| Volume flow ratio (V $N_2$ (new)/V (off-gas)) | 0.2 |

The Al content of the product was 6.8% by weight and the methyl/Al ratio was 0.96.

What is claimed is:

1. A process for preparing one or more alkylaluminoxanes immobilized on solid, particulate inert support material from one or more alkylaluminum compounds and water, comprising metering said one or more alkylaluminum compounds in one or more atomized or gaseous feed streams into a fluidized bed reactor containing therewithin said solid, particulate inert support material while maintaining said support material under fluidizing conditions with an inert gas stream, and providing water in said reactor, whereby said one or more alkylaluminum compounds and water react and form said one or more alkylaluminoxanes on said support material directly in said inert gas stream.

2. A process according to claim 1, characterized in that said water and said one or more alkylaluminum compounds are metered directly into the reactor.

3. A process according to claim 1, characterized in that said water and said one or more alkylaluminum compounds are provided in a molar ratio of water:alkylaluminum compounds, of from 0.5:1 to 1.3:1.

4. A process according to claim 1, characterized in that the alkylaluminum compound used is trimethylalumimum.

5. A process according to claim 1, characterized in that the support material is particles selected from the group consisting of $Al_2O_3$, MgO, $SiO_2$ and mixtures thereof and having particle sizes of 1–300 microns, surface areas of 10–1000 $m^2/g$, pore volumes of 0.5–3 $cm^3$ and water contents of 0–15% by weight.

6. A composition of matter which is one or more alkylaluminoxanes immobilized on solid, particulate inert support material prepared by a process comprising metering one or more alkylaluminum compounds in one or more atomized or gaseous feed streams into a fluidized bed reactor containing therewith a solid, particulate inert support material while maintaining said support material under fluidizing conditions with an inert gas stream, and providing water in said reactor, whereby said one or more alkylaluminum compounds and water react and form said one or more alkylaluminoxanes on said support material directly in said inert gas stream.

7. A composition of matter as claimed in claim 6, characterized in that 5–40% by weight of aluminum in the form of aluminoxanes is fixed on the support material.

8. A process according to claim 1, characterized in that the reactor is maintained at a pressure of from 1–20 bar.

9. A process according to claim 1 wherein the water is provided as surface hydration on the support material.

10. A process according to claim 1 wherein the water is provided by feeding a stream thereof into said reactor.

11. A process according to claim 1 wherein said process is carried out free of any solvents.

* * * * *

UNITED STATES PATENT AND TRADEMARK OFFICE
CERTIFICATE OF CORRECTION

PATENT NO. : 5,534,474
DATED : July 9, 1996
INVENTOR(S) : Ralf-Jurgen Becker, et al.

It is certified that error appears in the above-indentified patent and that said Letters Patent is hereby corrected as shown below:

Column 3, line 59: "Makromolo" should read --Makromol.--.

Signed and Sealed this

Twenty-ninth Day of April, 1997

Attest:

BRUCE LEHMAN

Attesting Officer

Commissioner of Patents and Trademarks